United States Patent [19]

Slaker

[11] 4,265,545
[45] May 5, 1981

[54] MULTIPLE SOURCE LASER SCANNING INSPECTION SYSTEM

[75] Inventor: Frank A. Slaker, Norwalk, Conn.

[73] Assignee: Intec Corporation, Trumbull, Conn.

[21] Appl. No.: 61,451

[22] Filed: Jul. 27, 1979

[51] Int. Cl.³ .................................... G01N 21/89
[52] U.S. Cl. ................................ 356/431; 250/572
[58] Field of Search ............................. 356/237–239, 356/431, 407, 445–448, 435; 250/571, 572, 339; 350/6.8; 174

[56] References Cited

U.S. PATENT DOCUMENTS

| 3,510,658 | 5/1970 | Rabedeau | 250/578 X |
| 3,843,890 | 10/1974 | Anthony, Jr. et al. | 250/227 X |
| 3,866,054 | 2/1975 | Wolf | 250/562 |
| 3,900,265 | 8/1975 | Merlen et al. | 250/572 X |
| 3,980,891 | 9/1976 | Slaker | 250/563 |
| 3,992,111 | 11/1976 | Roulier et al. | 356/431 |

Primary Examiner—John K. Corbin
Assistant Examiner—Bruce Y. Arnold

Attorney, Agent, or Firm—Parmelee, Johnson, Bollinger & Bramblett

[57] ABSTRACT

A laser scanning flaw direction inspection system is provided for simultaneously scanning a plurality of laser sources across a moving web of material being inspected. The plurality of laser beams are simultaneously scanned utilizing a common scanning apparatus. Laser beam radiation from the plurality of laser sources is collected from the web of material being inspected and detected for generating signals based on the integrity of the radiation applied to the detector from the material being inspected. The plurality of laser sources are preferably of different wave lengths, may have different spot sizes and may be separated by a fixed distance in either the scanned direction or in the direction of web travel. By providing such flexibility in size, positioning and wavelength, and using optical filters to separate the signals related to each of the sources, different types of flaws as well as different information may be generated which would not be possible using a single source system.

5 Claims, 5 Drawing Figures

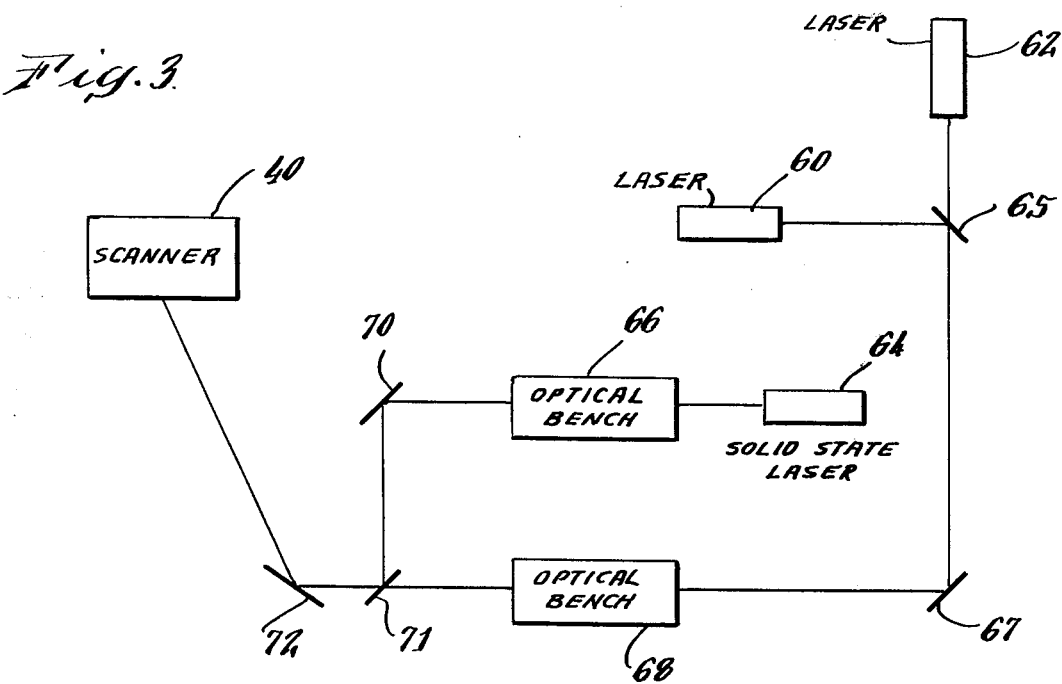
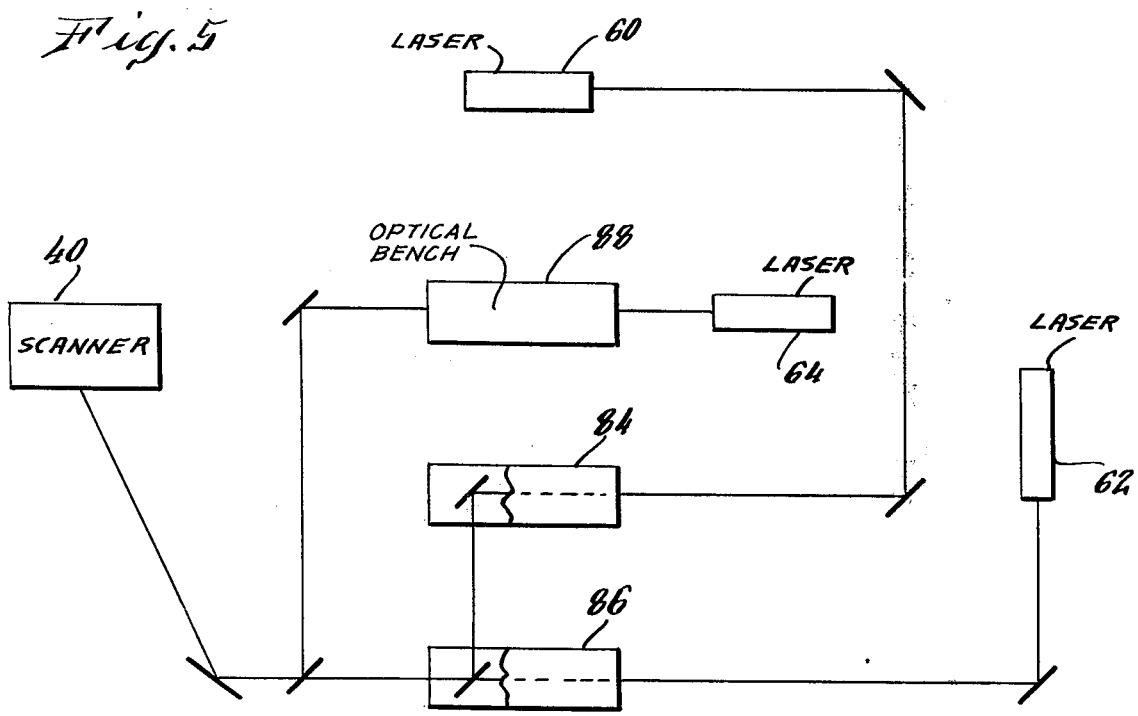

MULTIPLE SOURCE LASER SCANNING INSPECTION SYSTEM

BACKGROUND OF THE INVENTION

This invention relates to laser scanning flaw detection systems for the detection of flaws on a moving web of material, and more particularly to such a system in which a plurality of laser sources are simultaneously scanned across a moving web of material being inspected employing a common scanning means.

U.S. Pat. Nos. 3,900,265 entitled "Laser Scanner Flaw Detection System" and 3,980,891 entitled "Method and Apparatus for a Rotary Scanner Flaw Detection System", which patents are assigned to the assignee of the present invention, are illustrative of the type of system to which the present invention relates. In the aforesaid systems, flaws are detected in the material being examined by repetitively scanning a source of radiation in the form of a laser beam across the surface of material. The laser radiation is reflected, transmitted or scattered from the material depending upon the characteristics of the material being inspected. The laser radiation is picked up from the material by a receiver having suitable detectors such as photomultiplier tubes therein. At any instant in time during the scan, the photomultiplier output varies with the reflectivity, transmissivity or scattering properties of the spot on the material upon which the laser beam is impinging. Deviations in the signal from a normal characteristic signal provide a means for indicating that flaws exist in the material.

Another rotary scanner flaw detection system in U.S. Pat. No. 3,866,054 entitled "Defect Size Discriminator Circuit for Web Inspection System" illustrates the use of a receiver for picking up the radiation from the scanned web comprising a radiation conducting rod which conveys laser beam transmitted or reflected radiation from the material to a photomultiplier tube positioned on the end of the rod. A diffusing stripe is positioned in the rod so that when the radiation is applied thereto from the material being inspected, the radiation is dispersed within the rod causing internal reflection therein, thereby transmitting the radiation through the rod to the photomultiplier tube positioned on the end thereof.

In the aforesaid systems after signals have been generated in accordance with the intensity of radiation applied to the detectors from the material being examined, such signals are processed in electronic processing circuitry to identify the flaws in the material as well as provide other information with respect to such flaws such as their position on the material, the relative size of the flaws, whether the same flaws reoccur, identifying and not counting the occurrence of the same flaw in the material on subsequent scans of the material, counting the flaws in a prescribed manner, etc.

Although the use of a single scanning beam has proved very successful in inspecting webs of material quickly and efficiently, the use of a single scanning beam in some respects provides limited information with respect to the type and characteristics of a particular type of flaw. Certain defects do not lend themselves to detection by a single source, for example, if the source is not of a proper wave length to be reflected, transmitted or scattered by the flaw which is to be detected. Furthermore, any size or shape information would of necessity have to be generated by several passes of the same beam over the flaw of interest with the information being stored and compared on subsequent scans which procedure adds to the uncertainty in the detection and correlation process.

SUMMARY

It is an object of the present invention to provide a new and improved method and apparatus for the inspection of moving webs of material which has many distinct advantages over single source systems formerly employed by providing different as well as a greater amount of information with respect to the material being examined.

A further object of this invention is to provide a new and novel laser scanner flaw detection system which is capable of simultaneously detecting different types of flaws.

Still a further object of this invention is to provide a new and improved laser scanning flaw detection system which provides inherent real time redundancy thereby producing higher certainty in the flaw detection process.

Still a further object of this invention is to double the scan rate of the system by interlacing the scans of two sources in a down web direction.

Still another object of this invention is to provide a new and improved laser scanning flaw detection system in which real time comparisons are made with respect to flaw information eliminating the necessity for storing and comparing flaw information as is utilized in single source prior art systems.

Still another object of this invention is to provide a new and improved laser scanning flaw detection system which can automatically determine the optimum source for examination of a material.

In carrying out this invention in one illustrative embodiment thereof, a multiple source laser scanning inspection system is provided for detecting flaws in a web of moving material by simultaneously scanning a plurality of laser beams utilizing a common scanning means across the moving web of material being inspected. Receiver means are provided for collecting laser beam radiation from the web of material being inspected. The receiver means includes selective detector means coupled thereto for generating signals based on the intensity of the radiation applied by the receiver to the detector. The laser beams in accordance with various aspects of this invention may have different wavelengths, different spot sizes and/or may be separated by a fixed distance in the scan direction or in the direction of web travel. The detectors may be selectively sensitive to the different wavelengths of the laser beams in order to provide precise location information of the occurrence of a flaw on the material in accordance with the position of the impingement of a particular source on the material.

Advantageously, by using different wavelengths and different spot sizes, different types of flaws which would not be detected utilizing a single source may be detected by using the multiple sources. Also, the precise location of the multiple flaws can be reported. Furthermore, a common light collection system or receiver can be employed with appropriate optical filters to separate the signals related to each type of source. By separating the sources by a fixed distance in the scan direction, redundancy is obtained which provides greater certainty in the flaw detection process than would be obtainable from a single source. By separating the sources in web direction movement, real time occurrences of flaws can be immediately noted when two detections occur simultaneously which would normally require, in the use of a single beam, the storage of the first occurrence of the flaw compared with a second occurrence of the flaw on a subsequent scan of the same area. The multiple beam system eliminates this uncertainty. Furthermore, certain products are best examined for flaws when illuminated by a select wavelength which is made easy by the presence of a multiple source in which the magnitude of the signals will automatically determine the superior source for the examination for that particular product.

BRIEF DESCRIPTION OF THE DRAWINGS

The invention, together with further aspects, objects and advantages thereof, will best be understood from the following description taken in connection with the accompanying drawings.

FIG. 3 is a schematic illustration of another embodiment of the multiple source laser scanning inspection system in accordance with the present invention.

FIG. 5 is a schematic diagram illustrating three laser sources each of which is capable of being separately focused and scanned simultaneously in accordance with the present invention.

DESCRIPTION OF THE PREFERRED EMBODIMENTS

Figure 1:
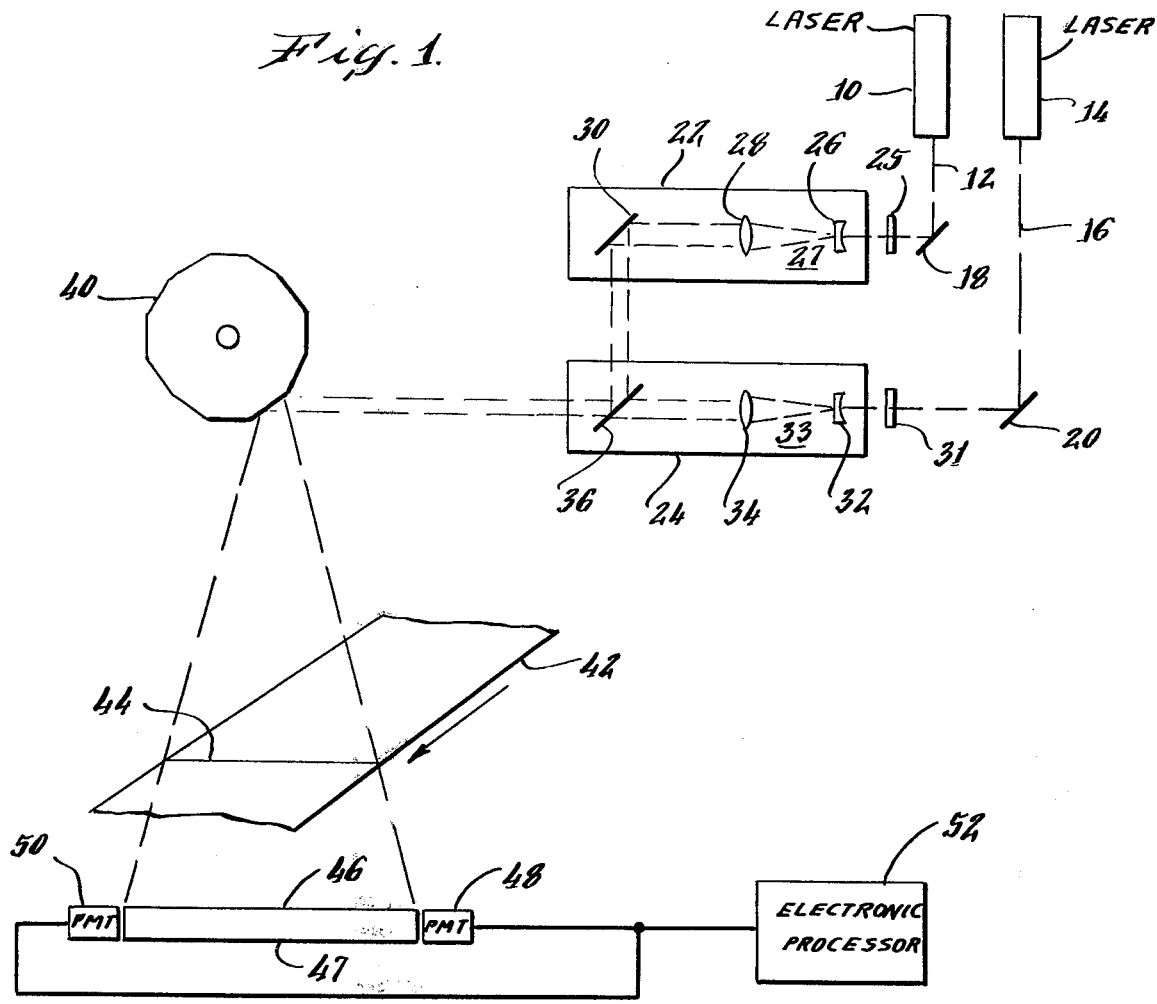
FIG. 1 is a schematic illustration of the multiple source laser scanning inspection system embodied in the present invention.

In the following description, like elements will bear the same reference numerals. Referring now to FIG. 1 suitable laser sources 10 and 14 generate laser beams 12 and 16, respectively which are applied via folding mirrors 18 and 20 to light forming optical benches 22 and 24, respectively. After the laser beam 12 passes through a focusing beam expander in the optical bench 22, it is reflected by silvered mirror 30 and applied to a dichroic element 36 in the optical bench 24. The laser beam 16 after passing through a focusing beam expander 33 in the optical bench 22 is also applied to the dichroic 36 and it along with the laser beam 12 are applied to a scanner 40.

The scanner 40 is a conventional multi-faceted mirrored surface polygon which is illustrated in FIG. 1 as having twelve facets. It will be appreciated that the scanner 40 may comprise any means which functions to scan the laser beams across the surface of the material to be inspected such as an oscillating mirror, a rotating mirror, a multi-faceted mirrored drum or any other suitable deflection apparatus. The scanner 40 performs the function of scanning the laser beams 12 and 16 simultaneously and repetitively across a web or sheet of material 42 being inspected which is continuously moving in the direction shown by the arrow on the drawing. The beams trace a scanning line 44 across the web of material 42. If the beams are offset in the direction of web travel, a plurality of lines 44 are scanned simultaneously thereacross.

Light or laser beam radiation transmitted through the web 42 is applied to a receiver 46 which is illustrated in FIG. 1 as a radiation conduction rod 46. Suitable optical means such as a pair of cylindrical lenses (not shown) may be used to direct the light from the web 42 to the light conducting rod 46. The radiation conducting rod 46 has a diffused stripe 47 thereon for dispersing the radiation within the rod to prevent it from passing through the rod or being reflected directly back out of the rod. Accordingly, radiation received from the web by the rod 46 is internally reflected down the rod to suitable detectors 48 and 50, such as photomultiplier tubes, which detect the light applied thereto. The output of the detectors 48 and 50 are applied to an electronic processor 52 which performs the function of discriminating, counting, sorting, etc. the flaws which exist in the material being examined. At any given instant in time during the scan, the detectors 48 and 50 provide an output which is proportional to the transmission of the spot of laser light on the material 42 on which the laser beams are impinging. Flaws occurring in the material being inspected change the output of the detectors 48 and 50 due to the transmissive properties of the material thereby providing a means for indicating flaws on the material. The signals are applied to the electronic processor 52 which may include one or more flaw discriminators for detecting and further processing the flaws in the material.

The illustrative system shown in FIG. 1 is a transmission system in which the receiver 46 collects radiation passing through the web and is shown in this form for ease of illustration. It should be appreciated that a reflective system may be employed and in such form the receiver 46 would be positioned above the web 42 in order to receive radiation reflected from the surface of the web 42. Whether a transmission or a reflective system are employed will depend on the type of material being inspected as well as the type of flaws which are desired to be detected. Accordingly, the use of the type of system either transmission or reflection will depend upon a particular application.

The optical benches 22 and 24 perform the function of focusing the laser beams 12 and 16, and generally may include a two lens system. The focusing beam expander 27 and 33 of the optical benches 22 and 24, respectively include planoconcave negative lenses 26 and 32 and duplex convex lenses 28 and 34, respectively. The expanded and focused beam 12 is applied from the optical bench 22 via the silvered mirror 30 to the dichroic 36 of optical bench 34 while the focused beam 16 is simultaneously applied to the dichroic element 36 through the beam expander 33. The negative lens elements 32 and 26 are adjustable allowing for the control of spot size and permitting the use and scanning of beams having a different spot size. Polarizers 25 and 31 may also be employed for adjusting the power of the beam.

Figure 2:
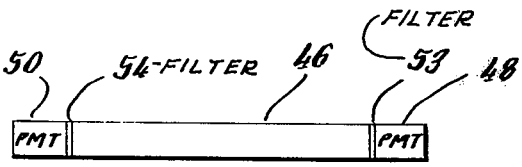
FIG. 2 is a front elevational view illustrating one type of receiver which may be employed in the present invention when two different wavelength laser beams are employed.

While the system illustrated would have benefits even for the case where the sources 10 and 14 have the same wavelength, maximum benefits are obtained when the sources have different wavelengths. In the case where different wavelengths are employed a common light collection receiver can be employed as illustrated in FIG. 2 with separate optical filters 53 and 54 utilized to separate the signals related to each of the sources. Alternatively, the detectors 48 and 50 may themselves be wavelength sensitive. Accordingly, by using selective detectors either filtered or otherwise selective, different types of flaws as well as their locations along the scan line may be identified. Since many inspection systems require the reporting of the precise location of the flaw, the common scanning apparatus insures that function for both sources when said sources are selectively identifiable.

This system may also be employed for the detection of certain types of flaws which is best done with a very small spot. One of the laser sources can be focused for this purpose. By the same token, other types of flaws may best be detected with a larger spot or an ellipse. The second source can be conditioned to meet this requirement and since different wavelengths are employed, the flaws may be simultaneously selectively detected and processed utilizing the same electronic processing circuitry.

Merely as examples for the two wavelength application, the laser source 10 may be a helium-neon laser generating a beam 12 in the wavelength 6328 Angstroms which is red light while laser source 14 generating a laser beam 16 may be an argon source which may be tuned to a blue wavelength of 4880 A or a green wavelength of 5145 A. Other types of lasers may be utilized to generate other wavelengths and the type of laser utilized will depend upon the application.

FIG. 3 illustrates the use of three laser sources 60, 62 and 64. The laser sources 60 and 62 are applied via a dichroic element 65 to a mirror 67 through the optical bench 68, dichroic element 71 and off a mirror 72 to the scanner 40. Another laser source 64 illustrated in the form of a solid state laser is applied via the optical bench 66 off a mirror 70 and dichroic 71 to the mirror 72 and onto the scanner 40 where all three laser sources 60, 62 and 64 are simultaneously scanned across the material to be examined using common scanner 40. The solid state laser 64 may be an infrared source having a wavelength of 820 nanometers. The optical bench 66 may employ a microscope objective for collimating the infrared laser source 64. In the detection system, an infrared detector may be employed.

Figure 4:
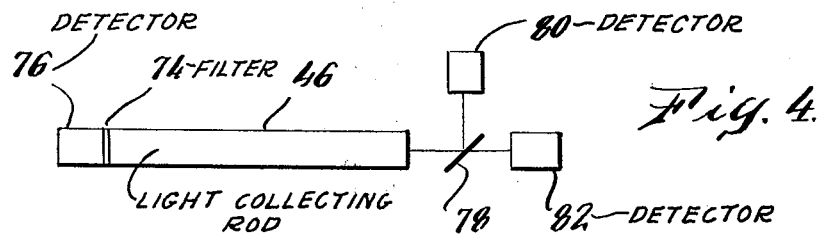
FIG. 4 is a front elevational view of another form of receiver which may be employed with the system illustrated in FIG. 3 in which three selective detectors are employed.

FIG. 4 illustrates a receiver arrangement for separately detecting the three different sources which include detectors 76, 80 and 82. A filter 74 is interposed between the radiation conducting rod 46 and the detector 76 to make the detector selective to a particular wavelength while a dichroic element 78 is positioned on the other end of the light collecting rod 46 to selectively apply different wavelengths of the collected radiation to detectors 80 and 82 thereby providing separate detectors for each wavelength. It will also be apparent that a dichroic element and two detectors may be employed in place of detector 76 and filter 74 in order to use four wavelengths and to separately detect them.

FIG. 5 illustrates the use of three laser sources 60, 62 and 64 each of which have separate optical benches 84, 86 and 88, respectively in order to provide separate and independent focusing of each beam. This configuration as well as others may be employed in accordance with the requirements of the application in which the inspection system is to be utilized.

The advantages obtained by using different spot size and different wavelengths for detecting different types of flaws and being able to accurately determine their location on the web of material being scanned has already been pointed out. Other distinct advantages are also available. For example, the plurality of sources may be utilized for generating the same spot size except that the spots are separated in the scan direction by a fixed distance. Such a system by providing multiple spots which scan the same area provide a redundancy which insure higher certainty of flaw detection than scanning the flaw by a single source system.

Another distinct advantage can be realized by separating the laser beam spots in the web travel direction. For example, in U.S. Pat. No. 3,900,265 electronic processing is provided which counts a flaw occurring on separate scans in the same position as one flaw. In order to do so the flaw information must be stored and compared with flaw information received from successive scan lines. By employing the present invention, such a flaw would be counted only if two or more detections occur simultaneously such that the correlations are in real time. Any uncertainty in storing and correlating the stored data is thus eliminated.

Among other advantageous uses of the multiple sources at different wavelengths is color detection. Since certain products are best examined for flaws when illuminated by a selected wavelength, the presence of multiple sources could be utilized to automatically determine which source is optimum for the inspection of that particular material and that particular source could be utilized for processing the flaws in the material so inspected. Many additional applications will benefit from the flaw detection process utilizing multiple sources and accordingly, the above examples are merely illustrative.

Since other changes and modifications varied to fit particular operating requirements and environments will be apparent to those skilled in the art, the invention is not considered limited to the examples chosen for purposes of illustration, and covers all changes and modifications which do not constitute a departure from the true spirit and scope of this invention.

What is claimed is:

1. A multiple source laser scanning inspection system for scanning a moving web of material with a plurality of laser sources and detecting flaws in a web of moving material being inspected in accordance with the characteristics of the laser light emanating therefrom comprising:

a plurality of laser sources for generating a plurality of laser beams, common scanning means for simultaneously scanning said plurality of laser beams across said moving web of material being inspected, optical means for directing said plurality of laser beams onto said common scanning means, receiver means for collecting laser beam radiation, applied by said plurality of laser beams from the web of material being inspected, and detector means coupled to said receiver means for generating signals based on the intensity of said radiation applied thereto by said receiver means, said signals including characteristics associated with each of said plurality of laser beams and said signals being used to detect and characterize flaws in said material.

2. The multiple source laser scanning inspection system set forth in claim 1 wherein said laser sources have different wavelengths.

3. The multiple source laser scanning inspection system set forth in claims 1 or 2 in which said laser beams have different spot sizes.

4. The multiple source laser scanning inspection system set forth in claims 1 or 2 in which said laser sources are separated by a fixed distance in the scan direction.

5. The multiple source laser scanning inspection system set forth in claims 1 or 2 in which said laser sources are separated by a fixed distance in the direction of web travel.

* * * * *